United States Patent
Shadan

(10) Patent No.: US 7,875,869 B1
(45) Date of Patent: Jan. 25, 2011

(54) APPARATUS FOR SANITIZING FEET OF PERSONS ENTERING A HOME

(76) Inventor: Kamyar Shadan, P.O. Box 144, Tiburon, CA (US) 94920

( * ) Notice: Subject to any disclaimer, the term of this patent is extended or adjusted under 35 U.S.C. 154(b) by 336 days.

(21) Appl. No.: 12/290,626

(22) Filed: Nov. 1, 2008

(51) Int. Cl.
*A61L 2/10* (2006.01)
*G01N 21/33* (2006.01)

(52) U.S. Cl. .............. 250/504 R; 250/492.1; 250/365; 422/24; 422/186.3; 607/88; 607/94

(58) Field of Classification Search ........... 250/504 R, 250/365, 492.1; 422/24, 186.3; 607/88, 607/94

See application file for complete search history.

(56) References Cited

U.S. PATENT DOCUMENTS

| | | | |
|---|---|---|---|
| 5,505,904 A | 4/1996 | Haidinger | |
| 5,652,991 A | 8/1997 | Kashani | |
| 5,661,645 A | 8/1997 | Hochstein | |
| 5,712,468 A | 1/1998 | Ace | |
| 5,786,598 A | 7/1998 | Clark | |
| 6,749,806 B2 | 6/2004 | Koji | |
| 7,306,620 B2 * | 12/2007 | Cumbie | 607/88 |
| 2008/0008620 A1 | 1/2008 | Alexiadis | |
| 2008/0310996 A1 * | 12/2008 | Kim et al. | 422/24 |
| 2009/0065716 A1 * | 3/2009 | Ullman | 250/504 R |
| 2009/0314308 A1 * | 12/2009 | Kim et al. | 134/1 |
| 2010/0193709 A1 * | 8/2010 | Dalton | 250/504 R |

* cited by examiner

*Primary Examiner*—Nikita Wells
(74) *Attorney, Agent, or Firm*—Robert Nathans

(57) ABSTRACT

Apparatus is provided, for sanitizing feet of persons entering a particular area, such as a residential area, having a platform for transmitting sanitizing ultraviolet light to feet of persons standing upon upper portions of the platform, a germicidal light source for directing sanitizing UV-C ultraviolet light through upper portions of the platform, a power supply for energizing the germicidal light source, a switching device coupled between the power supply and the germicidal light source for energizing the germicidal light source and wherein the switching device energizes the germicidal light source in response to the presence of the person positioned upon upper portions of the platform. The germicidal ultraviolet light source includes one or more elongated bulbs, or one or more elongated linear arrays of solid state devices and a central light reflective wall portion is positioned to enhance support of the upper portions of said platform.

19 Claims, 1 Drawing Sheet

APPARATUS FOR SANITIZING FEET OF PERSONS ENTERING A HOME

BACKGROUND OF THE INVENTION

Many persons residing in a home, apartment or other residence dislike having visitors bring dirt or mud carried on the visitor's soles of shoes into their residences. Thus, many of such persons request that visitors remove their shoes at the entranceway of the residences before entering the residences. Furthermore, people are becoming more interested in keeping their residences free of germs.

Many patents disclose methods for sanitizing various surfaces by employing ultraviolet light but our novelty search did not find prior art involving applying ultraviolet sanitizing light to a person's feet.

BRIEF SUMMARY OF PREFERRED EMBODIMENTS OF THE INVENTION

It is believed desirable to provide an apparatus at the entranceway of a residence or other enclosed area for encouraging, sanitizing their shoes before they enter the area with them on, or prompting and conditioning persons entering the residence to remove their shoes, to leave them at the entranceway so as not to track dirt into the residence, and additionally, after removal of the shoes, have them stand on an upper surface of our apparatus that directs germicidal ultraviolet light at the underside of the visitors' feet to kill germs that could otherwise be deposited in various areas within the residence during the visit.

The preferred apparatus for performing this dual function, includes a platform for directing sanitizing ultraviolet light at the feet of persons standing upon upper portions of the platform, a germicidal light source for directing sanitizing ultraviolet light in the germicidal range, preferably including (UV-C), through the upper light transmitting portions of the platform, a power supply, and a switching device, coupled between the power supply and the germicidal light source for energizing the germicidal light source in response to the presence of a visitor standing on the platform. The preferred light source has two sections associated with the left and right foot of the person entering the residence.

DRAWING DESCRIPTIONS

Other features of the invention will become more apparent upon study of the following description taken in conjunction with the drawings in which.

DETAILED DESCRIPTION OF PREFERRED EMBODIMENTS OF THE INVENTION

Platform 1 is provided for transmitting sanitizing ultraviolet light to feet of persons positioned upon upper portions of the platform. A germicidal light source can include a single elongated germicidal bulb or a pair of bulbs or linear LED arrays 2a and 2b for directing sanitizing ultraviolet light in the germicidal range through the upper portion 11 of the platform that consists of quartz or other UV-C light transmitting plastics.

Figure 1:
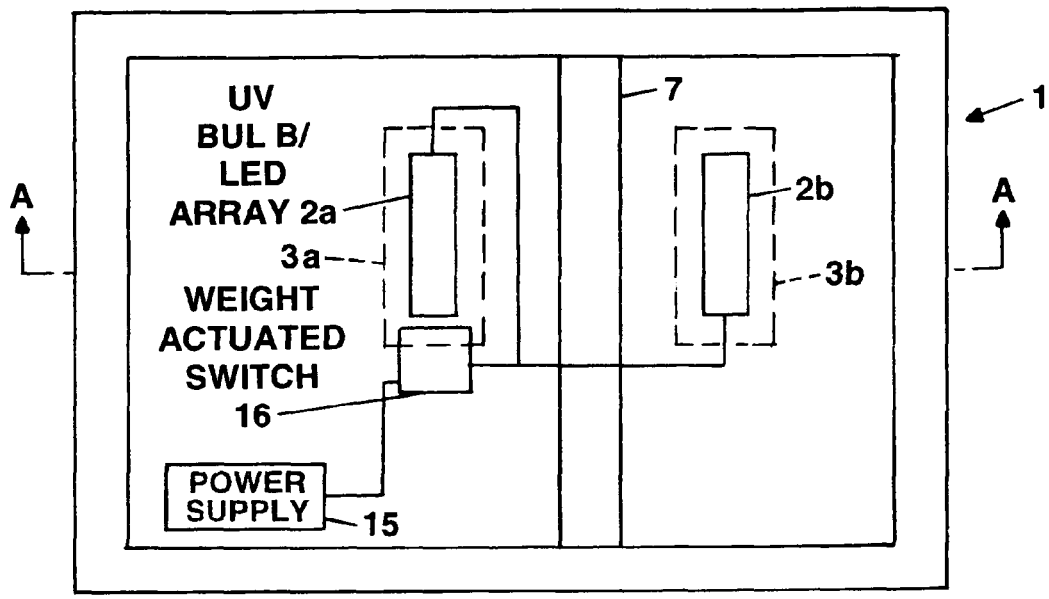
FIG. 1 shows a schematic view of the preferred apparatus.

A power supply 15 shown in FIG. 1 is provided for energizing the germicidal light source, and a switching device 16, coupled between the power supply and the germicidal light source is provided for energizing the germicidal light source in response to the presence of a person 9 standing upon upper portions 11 of the platform. The switching device is preferably actuated in response to a person's weight exerted against the switching device. Such a switching device that is incorporated within a mat, is disclosed in U.S. Pat. No. 3,821,500 issued to Newman on Jun. 28, 1974.

The switching device is preferably positioned within a subscribed area associated with the upper portions of the platform, thereby to facilitate proper positioning of a visitor's feet upon the upper portions and over the light source components. More specifically, rectangular indicia 3a and 3b can be present upon the upper plate 11 to aid in having the visitor place his feet over the elongated pair 2a and 2b of bulbs or LED arrays, preferably after removal of his shoes. A small flat switching device 16 could be placed within one or both of the rectangular indicia 3a and 3b upon or within upper portions of the platform. If the visitor's feet while standing on the upper platform plate 11 are not within the rectangular indicia, the light will not go on, thus signaling to him to move his feet into the rectangular indicia to receive the UV-C illumination. However, the apparatus may be used without removal of the visitor's shoes.

Figure 2:
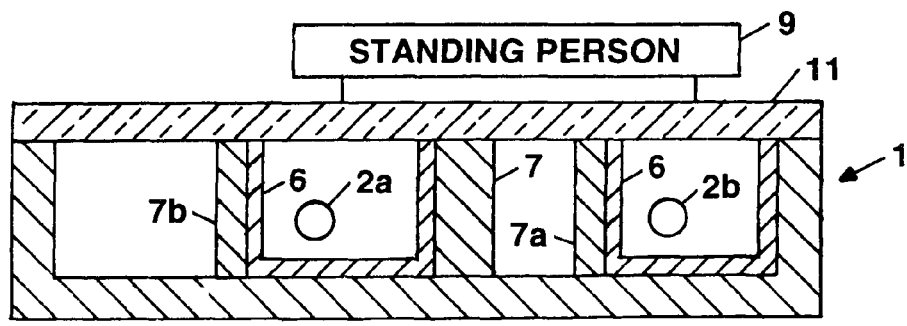
FIG. 2 shows a sectional view A-A through the apparatus of FIG. 1.

In FIG. 2, a central wall portion 7 is positioned between the aforesaid pair of elongated bulbs or elongated linear arrays of solid state devices (e.g. LEDs), to enhance support of the upper portion 11 of the platform. Additional support walls 7a and 7b may also be positioned to give added support to the upper portion 11 which can constitute a quartz UV transmissive plate. The inner wall portions 7, 7a and 7b may be coated with a highly reflective metallic coating 6 such as aluminum or chromium, thus enhancing the scatter effect of the light in the interests of greater uniformity of intensity of light passed through upper portion 11.

Figure 3:
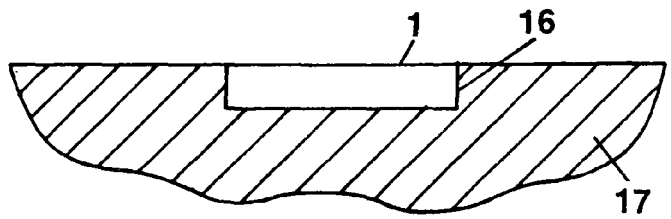
FIG. 3 shows the apparatus 1 recessed within a floor portion of an entranceway of an enclosed area, typically a residential area.

As shown in FIG. 3, the platform 1 constituting the aforesaid apparatus may be positioned within a recess 16 formed within a floor portion 17 of the entrance portion, reducing possibility of persons tripping over the apparatus.

The preferred spectral output UV is weighted at 253.7 nanometers. Ultraviolet light at this wavelength is germicidal but only penetrates slightly into the skin, confining its action to the skin surface layers. Ultraviolet light as this wavelength is not as invasive as exposure to sun light with its broad spectrum of ultraviolet wavelengths. As stated in Gadgil U.S. Pat. No. 6,602,425, germicidal ultraviolet light sources may be any one of a number of types, such as low, medium or high-pressure mercury lamps or xenon arc lamps, or a solid-state UV source (e.g., an LED or laser), depending upon availability. This wavelength has been found to be particularly useful in the destruction of pathogenic micro-organisms. Mirapol et al., U.S. Pat. No. 4,952,812 teaches the use of a quartz plate for transmission of UV light predominately of a wavelength of 280-320 nanometers. Linear LED arrays and their power supply are disclosed in U.S. Pat. No. 5,661,645 to Hochstein.

While the preferred switching device is weight responsive, other switching devices can be utilized such as motion sensors e.g. those used in rest room hand drying apparatus, light beam interruptive sensors, e.g. light beam sensor switches such as those used in garage door openers, person presence detectors for arresting door motion. Even a manually operated switch may be used. The germicidal light source may include a plurality of solid state sources (e.g. light emitting diodes, lasers). The power supply could be a rechargeable battery or an AC/DC power supply.

The platform may take the form of a more conventional type of portable housing mat provided it contained UV light sources, if available, that could withstand the weight of a very heavy person standing on the mat.

While the enclosed area would commonly be a residential home, other areas may find the use of the apparatus beneficial. Medical clinics, laboratories, even transportation related areas may be suitable for the use of the apparatus of the invention. A sign adjacent the apparatus could be beneficial and could suggest that the visitor remove his shoes and stand upon the platform.

I claim:

1. Apparatus for sanitizing feet of persons entering a particular area of an enclosure having:
   (a) a platform for transmitting sanitizing ultraviolet light to feet of persons positioned upon upper portions of said platform;
   (b) a germicidal light source for directing sanitizing ultraviolet light in the germicidal range through the upper portions of said platform;
   (c) a power supply for energizing said germicidal light source; and
   (d) a switching device coupled between said power supply and said germicidal light source for energizing said germicidal light source; wherein said switching device energizes the germicidal light source in response to the presence of said persons upon upper portions of said platform.

2. The apparatus of claim 1 wherein said switching device is actuated in response to a person's weight exerted against said switching device.

3. The apparatus of claim 2 wherein said germicidal light source includes one or more ultraviolet light generating lamps.

4. The apparatus of claim 2 wherein said germicidal light source includes a plurality of solid state sources.

5. The apparatus of claim 1 wherein said germicidal light source includes one or more ultraviolet light generating lamps.

6. The apparatus of claim 1 wherein said germicidal light source includes one or more solid state sources.

7. The apparatus of claim 1 wherein said switching device is positioned within a subscribed area associated with the upper portions of said platform, thereby to facilitate proper positioning of a visitor's feet upon said upper portions.

8. The apparatus of claim 1 wherein said germicidal light source includes one or more ultraviolet light generating lamps.

9. The apparatus of claim 1 wherein said germicidal light source includes a plurality of solid state sources.

10. The apparatus of claim 1 wherein said particular area is a residential area.

11. Apparatus for sanitizing feet of persons entering a particular area of an enclosure having:
    (a) a platform for transmitting sanitizing ultraviolet light to feet of persons positioned upon upper portions of said platform;
    (b) a germicidal light source for directing sanitizing UV-C ultraviolet light through the upper portions of said platform;
    (c) a power supply for energizing said germicidal light source;
    (d) a switching device coupled between said power supply and said germicidal light source for energizing said germicidal light source; and
    (e) wherein said switching device energizes the germicidal light source in response to the presence of said person upon upper portions of said platform.

12. The apparatus of claim 11 wherein said germicidal ultraviolet light source includes one or more elongated bulbs, or one or more elongated linear arrays of solid state devices.

13. The apparatus of claim 12 wherein a central wall portion is positioned between a pair of elongated bulbs or a pair of elongated linear arrays of solid state devices, to enhance support of the upper portions of said platform.

14. The apparatus of claim 13 wherein said central wall portion and adjacent inner wall portions are coated with light reflective material.

15. The apparatus of claim 11 wherein said switching device is positioned within a subscribed area associated with the upper portions of said platform, thereby to facilitate proper positioning of a visitor's feet upon said upper portions.

16. The apparatus of claim 11 wherein said particular area is a residential area.

17. A method for thwarting the introduction of germs within an enclosed area whereby:
    (a) an apparatus is provided at an entrance portion of said enclosed area for sanitizing feet of persons entering a particular area, said apparatus having
    (a-1) a platform for transmitting sanitizing ultraviolet light to feet of persons positioned upon upper portions of said platform;
    (a-2) a germicidal light source for directing sanitizing ultraviolet light in the germicidal range through the upper portions of said platform;
    (a-3) a power supply for energizing said germicidal light source;
    (a-4) a switching device coupled between said power supply and said germicidal light source for energizing said germicidal light source; and
    (a-5) wherein said switching device energizes the germicidal light source in response to the presence of persons upon upper portions of said platform;
    (b) requesting a visitor to remove their shoes and thereafter stand upon said platform; and
    (c) in response to a visitor standing upon said platform, causing said switching device to electrically couple the power supply to said germicidal light source, thereby directing sanitizing ultraviolet light through the upper portions of said platform at the feet of said visitor.

18. The method of claim 17 including positioning said apparatus within a recess formed within a floor portion of said entrance portion, reducing possibility of persons tripping over the apparatus.

19. The method of claim 17 wherein said enclosed area is a residential area.

* * * * *